United States Patent
Timberg et al.

(10) Patent No.: US 9,833,203 B2
(45) Date of Patent: Dec. 5, 2017

(54) COMPRESSION DEVICE FOR X-RAY AND MECHANICAL IMAGING OF A BREAST

(71) Applicant: LU License AB, Lund (SE)

(72) Inventors: Pontus Timberg, Malmö (SE); Daniel Förnvik, Malmö (SE); Magnus Dustler, Hässleholm (SE); Sophia Zackrisson, Ystad (SE)

(73) Assignee: LU License AB, Lund (SE)

( * ) Notice: Subject to any disclaimer, the term of this patent is extended or adjusted under 35 U.S.C. 154(b) by 0 days.

(21) Appl. No.: 14/783,801

(22) PCT Filed: Apr. 11, 2014

(86) PCT No.: PCT/EP2014/057372
§ 371 (c)(1),
(2) Date: Oct. 9, 2015

(87) PCT Pub. No.: WO2014/167097
PCT Pub. Date: Oct. 16, 2014

(65) Prior Publication Data
US 2016/0051207 A1 Feb. 25, 2016

(30) Foreign Application Priority Data
Apr. 11, 2013 (SE) ........................ 1300265

(51) Int. Cl.
*A61B 6/00* (2006.01)
*A61B 6/04* (2006.01)

(52) U.S. Cl.
CPC .............. *A61B 6/04* (2013.01); *A61B 6/0414* (2013.01); *A61B 6/502* (2013.01); *A61B 6/5229* (2013.01); *A61B 6/54* (2013.01)

(58) Field of Classification Search
CPC .............................. A61B 6/0414; A61B 6/502
See application file for complete search history.

(56) References Cited

U.S. PATENT DOCUMENTS

2008/0043904 A1 2/2008 Hoernig
2008/0080668 A1* 4/2008 Kashiwagi ........... A61B 6/0414
378/37

(Continued)

FOREIGN PATENT DOCUMENTS

DE 10 2010 009011 A1 8/2011
JP 2009 285345 A 12/2009

OTHER PUBLICATIONS

Dustler, M., et al., "The Effect of Breast Positioning on Breast Compression in Mammography: a Pressure Distribution Perspective," Medical Imaging 2012: Physics of Medical Imaging, vol. 8313, pp. 83134M1-83134M6.

(Continued)

*Primary Examiner* — Dani Fox
(74) *Attorney, Agent, or Firm* — Christensen O'Connor Johnson Kindness PLLC

(57) ABSTRACT

The invention relates to a compression device (1) for assisting x-ray examination of an object. The compression device (1) comprises a support plate (3) adapted to receive thereon the object to be examined; a compression plate (4); and a displacement device (5) arranged to interact with the support plate (3) and the compression plate (4) to allow modification of the spacing (A) between the support plate (3) and the compression plate (4) to compress the object there between. A plurality of pressure sensors (13) are distributed across the support plate (3) and/or the compression plate (4) for sensing local pressure distribution across the compression area of the compressed object. The displacement device (1) is arranged to set and adapt the spacing (A) between the support plate (3) and the compression plate (4) angularly and linearly as a result of the sensed local pressure distribution across the compression area.

20 Claims, 3 Drawing Sheets

(56) References Cited

U.S. PATENT DOCUMENTS

| | | | | |
|---|---|---|---|---|
| 2010/0030078 A1* | 2/2010 | Mikami | ............... | A61B 6/0414 600/443 |
| 2013/0028373 A1* | 1/2013 | Den Heeten | ......... | A61B 6/0414 378/37 |
| 2014/0093034 A1* | 4/2014 | Takata | ................... | A61B 6/544 378/37 |

OTHER PUBLICATIONS

International Search Report dated Jul. 28, 2014, issued in corresponding International Patent Application No. PCT/EP2014/057372, filed Apr. 11, 2014.

* cited by examiner

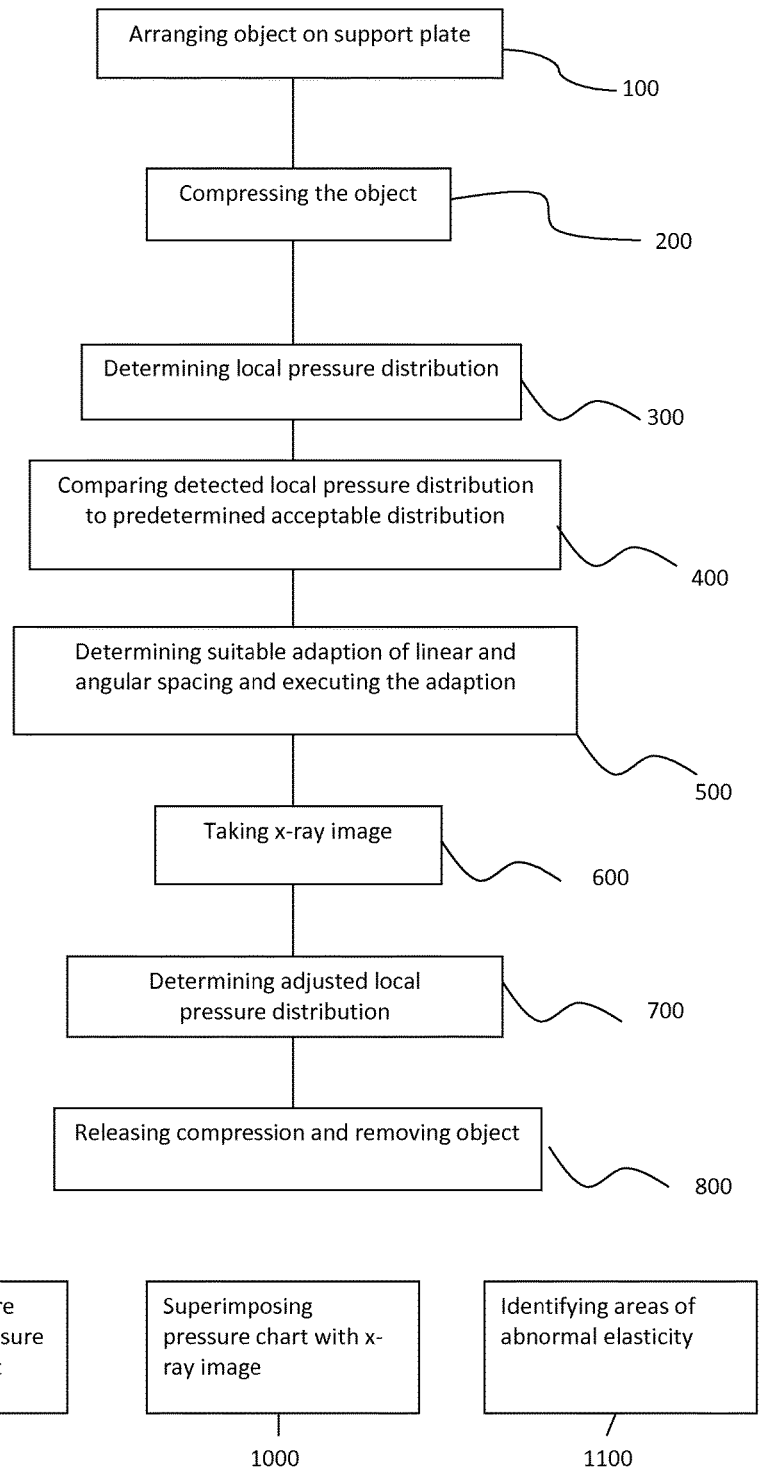

COMPRESSION DEVICE FOR X-RAY AND MECHANICAL IMAGING OF A BREAST

TECHNICAL FIELD

The present invention relates to a compression device and a method for assisting examination of an object using a field of penetrating radiation.

BACKGROUND

Mammography is the current imaging method of choice for breast cancer screening. However, it is a suboptimal technique in terms of breast cancer detection with up to 30% missed cancers reported in screening. Two important reasons for non-detection of cancer are the superimposed tissue when applying 2D imaging (mammography) to a 3D object (the breast), and certain cancer growth patterns and subtle differences in physical properties between some tumors and normal tissue. To reduce the superimposed tissue effect, breast tomosynthesis has been developed. Breast tomosynthesis employs a semi-3D technique that improves depth resolution by providing thin slices of the breast, using low dose levels of radiation similar to digital mammography.

In principle, a mammography apparatus for detecting malignant lesions in a breast comprises an x-ray source and an x-ray detector that cooperates for providing an x-ray image of the breast. The breast is inserted into a compression device wherein it is pressed by means of a paddle against the x-ray detector. By the compression, the breast is flattened in order of getting a proper x-ray image. By the compression, the image quality may be improved by increased breast tissue separation. Further, scattered radiation may be reduced and the radiation dose to the breast may be minimized. Mammographic imaging systems have undergone remarkable improvements, but the compression device has remained basically unchanged since modern mammography was introduced in the sixties.

A high attendance in a screening program is a key factor in order to achieve reduced breast cancer mortality. Still, according to studies, many women refrain from attending the screening due to the pain experienced during the breast compression.

In addition, the compression device is inefficient in terms of fixating the breast and providing proper breast compression. It is has been noted that generally high pressure is applied not only to the breast as such but also to the pectoral muscle and nearby tissues. Excessive applied force does not only cause unnecessary pain, but does also fail to reduce tissue thickness.

US 2013/0028373 A1 discloses one example dealing with this issue. The document suggests a solution wherein the mammography apparatus has a contact measuring unit for measuring the contact area between the breast and the paddle. At least one sensor is used to measure the force that is applied to the breast. The force together with the contact area provides the average pressure that is applied to the breast. The average pressure can then be controlled at a pre-established level so as to avoid un-necessary and avoidable pain during imaging.

SUMMARY OF THE INVENTION

It is an object of the present invention to provide an improved compression device reducing the experienced pain and unnecessary pain, whereby fewer women will refrain from screening.

Another object is to provide an improved compression device and image method that allows the compression to be directed to relevant parts of the body.

Yet another object is to provide improved imaging methods to increase the likelihood of detection of tumors.

According to a first aspect, these and other objects are achieved by a compression device for assisting examination of an object using a field of penetrating radiation, comprising a support plate adapted to receive thereon the object to be examined; a compression plate; a displacement device arranged to interact with the support plate and the compression plate to allow modification of the spacing between the support plate and the compression plate to compress the object there between; and a plurality of pressure sensors distributed across the support plate and/or the compression plate for sensing local pressure distribution across the compression area of the compressed object, wherein the displacement device is arranged to set and adapt the spacing between the support plate and the compression plate angularly and linearly as a result of the sensed local pressure distribution across the compression area.

The term penetrating radiation as used in this document should be interpreted as including x-rays.

Accordingly, the compression device of the present invention uses an adaptive pressure distribution system, whereby the current pressure distribution on the object, such as a breast, may be measured during the examination. Thereby a more dynamic compression allowing an adaptive pressure distribution is provided for.

According to the present invention, when an even load is applied to the breast the internal structures, with their different inherent elastic moduli, will give rise to internal pressures that can be imaged using pressure sensors. Relatively increased pressure levels can be found over malignant tumors. This imaging method is referred to as mechanical or tactile imaging.

Besides a breast thickness gradient that usually is decreasing from the chest wall to the nipple, other structures are present in the breast or close by that will affect the pressure distribution. The most prominent of these is the pectoral muscle, which is rather stiff compared to surrounding tissue and becomes even stiffer if the woman being examined is tense. A reduced compression force will not result in a substantial increase in breast thickness, indicating that force is not a good indicator of adequate breast compression. One does not strive for a uniform pressure on the breast as the components of interest are usually dense parenchymal tissue surrounded by fat where the fat requires less pressure to receive equal compression.

Therefore it is beneficial to be able to selectively distribute force over the breast based on the information gleaned from the plurality of pressure sensors.

A novel way of imaging the object, such as a breast, according to the present invention, is through mechanical imaging using the pressure distribution arising from breast compression with a compression plate. The term mechanical imaging should in the context of the application also include tactile imaging.

The invention allows x-ray imaging and mechanical imaging to be performed simultaneously during one and the same examination. Mechanical imaging can be used to visualize internal structures by sensing the pattern of mechanical stresses on the surface of an organ. Other organs that are suitable for palpation in order to detect disease are also well suited for this type of compression device and the invention is applicable on any other suitable organ in addition to the breast. The contrast in elastic stiffness between normal and abnormal breast tissue has been recognized, although mostly acquired ex-vivo.

Nevertheless, breast tissue is evidently non-linearly elastic, showing an exponential decrease in the rate of thickness reduction as a result of increasing pressure. By the relative change in stiffness, with strain level also varying with different tissue types, it is possible to differentiate malignant structures from normal breast tissue from a pressure distribution measurement made on the surface of a compressed breast, or in another embodiment of the present invention use the pressure image to add additional diagnostic information to the x-ray image.

By using a compression device that can map and regulate the pressure distribution over the compressed object, it is made possible to use an imaging principle based on the elastic properties of the tissues (mechanical imaging) which improves the likelihood of detecting tumors as compared to mammography alone.

The displacement device may at least partly be formed by the stand of a mammographic apparatus.

The compression plate and/or the support plate may be provided with electrically or pneumatically operated servos. By such servos, the angularity between the compression plate and the support plate may be altered dynamically according to the local pressure distribution detected by the plurality of pressure sensors.

The spacing between the support plate and the compression plate may be adapted angularly in at least two degrees of freedom. The angular adjustment may be made in at least two degrees of freedom simultaneously. The angular adjustment may be made as a pitch and or a roll. By allowing an angular adjustment in at least two degrees of freedom, the possibility of providing a suitable compression distribution across the object is enhanced. Thereby also the possibility of providing x-ray images of a high quality is enhanced. Further, the compression distribution may be adapted to the actual anatomy of the breast to be examined and also to specific areas of breast tissue. Thus a form of customization is offered.

The angular and linear spacing between the support plate and the compression plate may be arranged to be manually set and adapted. Thus, the operator may use information received in real time from the mammographic apparatus and the displacement device. The information may by way of example be presented to the operator on a display.

The compression plate may be segmented, the segments being individually operable based on information regarding local pressure distribution received from the pressure sensors. The segmentation allows a higher degree of adapting the pressure distribution to the anatomy of the woman to be examined or to certain areas of specific interest.

The displacement device may be arranged to dynamically set and adapt the angular and linear spacing between the support plate and the compression plate as a result of the sensed local pressure distribution. This may be based on real time information received from a controller. The controller may be integrated with the mammographic apparatus or be a controller dedicated to the control of the compression device and it displacement device.

The pressure sensors may be arranged as an array or a matrix. The array or matrix is arranged to cover the relevant surface area of the support plate or the compression plate. It is to be understood that the number of individual sensors included in such array or matrix depends on factors such as sensitivity, spatial resolution and accuracy. It is also to be understood that the pressure sensors may be arranged integrated in or detachable to the respective plate on the outer surface thereof or in a position proximate to the outer surfaces. The pressure sensors may be radio-opaque pressure sensors or radiolucent pressure sensors. By the sensors, the local pressure distribution may be measured and based on that information the pressure distribution in relation to the breast anatomy may be graphically mapped. Radiolucent pressure sensors have the advantage over radio-opaque sensors, in that they are allowed to be included in the mammographic field of view without impairing the x-ray image quality.

The pressure sensors may be disposable. Thereby they may be made cheap and be made to be discarded after a limited number of uses.

According to another aspect, the invention relates to a method of assisting examination of an object using a field of penetrating radiation, comprising: arranging the object to be examined in a compression device, the compression device comprising a support plate and a compressing plate and compressing the object there between; determining, by a plurality of pressure sensors distributed across the support plate and/or the compression plate, the local pressure distribution across the compression area of the compressed object; evaluating the determined local pressure distribution across the compression area in view of a pre-determined approved pressure distribution; and adapting the spacing between the support plate and the compression plate angularly and linearly as a result of the evaluated local pressure distribution.

The method offers a number of advantages previously discussed in view of the compression device. The advantages are equally applicable to the method and to avoid undue repetition, reference is made to the previous paragraphs. One drawback with prior art is that related modalities such as ultrasound elastography and magnetic resonance elastography may be employed diagnostically but limitations including deformation range, resolution and tissue anisotropy limit their sensitivity. By the present invention, it is made possible to perform mechanical imaging and use the same pressure image for both diagnostic purposes and for improving compression.

The method may further comprise the step of determining an adjusted local pressure distribution across the compression area of the compressed area after adapting the spacing.

The method may further comprise the step of visualizing the local pressure distribution and/or the adjusted local pressure distribution as a pressure distribution chart.

The method may further comprise the step of taking an x-ray image of the compressed object after adapting the spacing between the support plate and the compression plate.

The method may further comprise the step of superimposing the local adjusted pressure distribution chart with the x-ray image.

The method may further comprise the step of comparing pressure data collected when determining adjusted local pressure distribution with pre-defined information regarding tissue elasticity in order of identifying areas of abnormal elasticity in the tissue of the compressed object.

BRIEF DESCRIPTION OF THE DRAWINGS

Objects, features and advantages of the present invention will appear from the following detailed description of the invention, wherein embodiments of the invention will be described in more detail with reference to the accompanying drawings.

FIG. 2 discloses a flow chart describing the method according to one embodiment of the invention.

DETAILED DESCRIPTION

Embodiments of the present invention will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

In digital mammograms, breast compression is performed to improve image quality by increasing breast tissue separation and reducing scattered radiation, and to minimize the radiation dose to the breast, which is one of the most radiosensitive tissues of the human body. For these reasons, the breast is compressed as much as reasonably possible to a level just below the patient's pain threshold. In general, the more the breast volume is spread out in the two-dimensional mammogram, the more accurate the image interpretation will be. There may also be situations where it might be desired to provide as homogenous thickness of the breast as possible.

In breast tomosynthesis as well as in digital mammography, the breast must be fixated to avoid motion artifacts. However, the scan time in breast tomosynthesis may be as much as twenty seconds, which is much longer than in digital mammography. Since breast tomosynthesis is a semi-3D technique, it may benefit from a reduced compression due to better separation of the tissue in the depth direction. The reconstruction algorithm commonly used in breast tomosynthesis effectively compensates for the scattered radiation that occurs in the individual projections. For this reason, the greater thickness of the irradiated tissue (due to lower compression) does not negatively affect the scatter radiation proportion in the resulting breast tomosynthesis image.

Applied breast compression has been investigated in conjunction with digital mammography. However, the compression device was in that case proven to be very inefficient due to the fact that most pressure was applied to the chest wall and not really spreading the structures of the central breast as intended.

Figure 1:
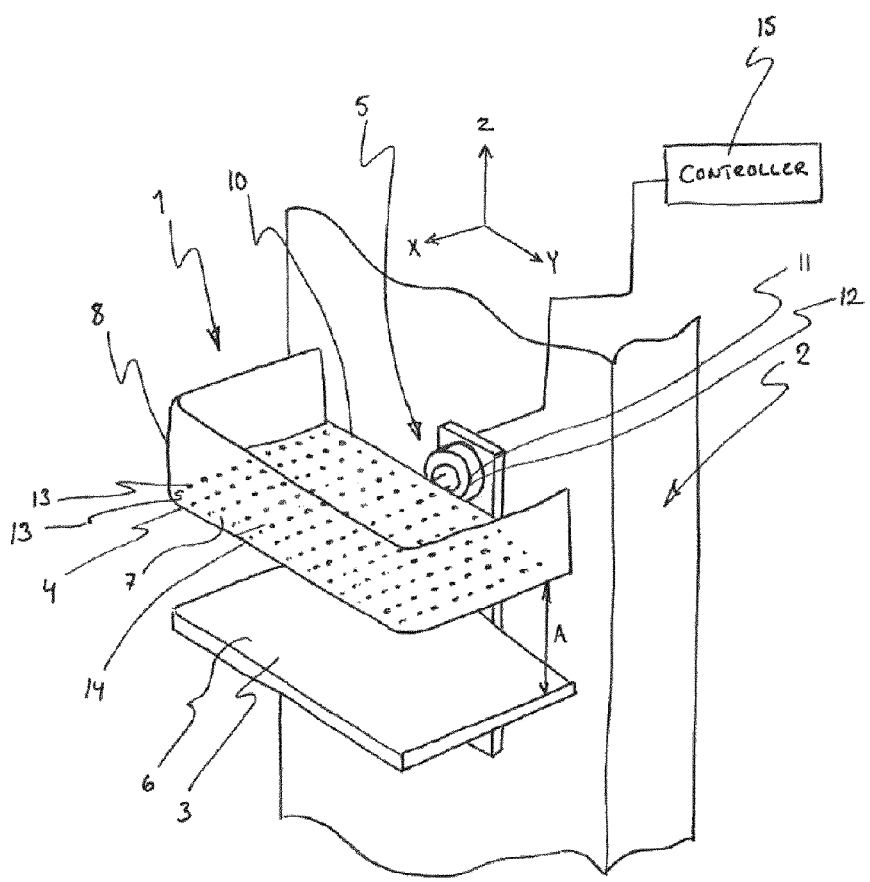
FIG. 1 discloses highly schematically a perspective view of a compression device according to one embodiment of the invention when mounted in a mammography device.

Now referring to FIG. 1, a perspective view of one embodiment the compression device 1 according to the invention is disclosed highly schematically. The compression device 1 is arranged in a mammographic apparatus 2.

The compression device 1 comprises a support plate 3, a compression plate 4, and a displacement device 5.

To facilitate the following description, the compression device 1 will be explained with the plates 3, 4 oriented with their main surfaces horizontally oriented, i.e. in the illustrated x-y plane. It goes without saying that the plates 3, 4 may be differently oriented, especially during use.

The support plate 3 comprises an essentially flat upper surface 6 adapted to receive an object to be examined. In the description to follow, the object will be described as a breast. It is to be understood that the invention should not be limited to a breast but could also apply to other body parts.

The support plate 3 is made of a solid material capable of supporting the breast (not disclosed). In an x-ray device (not disclosed) it covers the x-ray detector and is therefore constructed of a material suitable for x-ray transmission, such as a graphite. It may also by itself be the detector. The upper surface 6 is arranged facing a lower surface 7 of the compression plate 4.

The compression plate 4 comprises an essentially flat surface which in its most simple form is made of a PMMA (Polymethyl methacrylat), polycarbonate or carbon fiber or any other material suitable for transmission of x-rays. The material is preferably hard and durable. Further, it is advantageous if the material is transparent to facilitate proper orientation of the breast.

In the disclosed embodiment the compression plate 4 is disclosed as being roughly tray shaped with vertical wall portions 8 facing away from the mammographic apparatus 2 surrounding the essentially flat lower surface 7. The wall portions 8 may be used to ensure that no other body portions interfere.

The compression plate 4 may be arranged in segments (not disclosed), e.g., with a grid-like structure. Each segment may have force individually applied to it, in one embodiment by using servos or pneumatics to be described below. Further, each segment may be provided with its own array or matrix of pressure sensors.

The compression plate 4 and the support plate 3 are arranged with a spacing A between the upper surface 6 of the support plate 3 and the lower surface 7 of the compression plate 4. The spacing A may be controlled by moving either the support plate 3 and/or the compression plate 4 in view of each other to thereby allow insertion of the object to be examined, compressing the same, adjusting the spacing A and thus the degree of compression, and ultimately releasing the object. The support plate 3 and the compression plate 4 are moved in view of each other by the displacement device 5 to be described below.

The displacement device 5 is arranged to interact with the support plate 3 and the compression plate 4 to allow setting and adaption of the spacing A there between. The displacement device 5 is arranged to be connected either directly or indirectly to the mammographic apparatus 2. In the disclosed embodiment, the displacement device 5 is integrated with the stand 9 of the mammographic apparatus 2.

The displacement device 5 is arranged to the stand 9 of the mammographic apparatus 2 to allow a linear, vertical movement of the compression plate 4 in view of the compression plate 4, i.e. along the z-axis as illustrated.

In the disclosed embodiment, the compression plate 4 is provided at a rear edge portion 10 thereof with a coupling 11 via which it is connected to the displacement device 5. The coupling 11 allows an angular movement, i.e. tilting of the lower surface 7 of the compression plate 4 in view of the upper surface 6 of the support plate 3. The coupling 11, highly schematically illustrated, should preferably allow an angular movement in at least two degrees of freedom. The coupling 11 could by way of example be of a ball joint type or a disc joint type. The coupling 11 could be operated by electrical or pneumatic servos 12.

In the disclosed embodiment the lower surface 7 of the compression plate 4 is provided with a plurality of pressure sensors 13. In the disclosed embodiment, each sensor 13 is illustrated as a dot. It is to be understood that alternatively the plurality of sensors 13 may be arranged on the upper surface 6 of the support plate 3 or as yet another alternative both on the lower surface 7 of the compression plate 4 and the upper surface 6 of the support plate 3. The pressure sensors 13 are preferably arranged in a well defined pattern such as in an array or matrix 14. The array or matrix 14 is arranged to cover the relevant surface area of the support plate 3 and/or the compression plate 4. By relevant surface is meant the surface intended to be in contact with the object to be compressed.

The number of pressure sensors 13 included in the array or matrix 14 depends on factors such as sensitivity and accuracy of the used pressure sensors 13 and the desired pressure information respectively. The pressure sensors 13 may be arranged integrated in or detachable to the respective plate on the outer surface thereof or in a position proximate thereto.

The pressure sensors 13 may be disposable.

The pressure sensors 13 may be radio-opaque, so called force sensing resistor sensors, where the resistance of a circuit is a function of the applied pressure. Radio-opaque sensors will be seen as spots on the x-ray image.

Alternatively, the pressure sensors 13 may be so called radiolucent sensors. Radiolucent sensors have the advantage that they do not affect the diagnostic imaging task and are thin, flexible, precise and robust and suitable for inclusion in a sensor array, so that it becomes possible to obtain a good spatial resolution of the pressure distribution. The radiolucent sensors may be constructed from conductive polymers and/or very thin metal electrodes, which may, in one embodiment, be made from metals with a combination of low x-ray absorption and high conductivity, such as but not limited to chromium (Cr) and titanium (Ti). However, other types of sensors may also be used with the same result.

Other forms of piezoresistive sensors may also be used. In another embodiment of the present invention capacitive pressure sensors consisting of two thin conductive layers separated by some polymer or plastic material which will deform under pressure, thus changing the capacitance of the circuit as a function of the applied pressure, may be used.

In order to obtain good mechanical images, it is preferred that the pressure sensors should be sensitive and provide a high spatial resolution.

Each pressure sensor 13 is arranged to detect a local pressure applied thereto when being in contact with the object compressed between the compression plate 4 and the support plate 3.

The pressure sensors 13 are connected to a controller 15 adapted to receive information regarding detected local pressure from each individual pressure sensor 13. The controller 15 may be a part of the controller used in the mammographic apparatus 2 or be a separate controller suitable for communication therewith. It is advantageous that the controller 15 is additionally arranged to control the displacement device 5.

The controller 15 is adapted to receive information from the plurality of pressure sensors 13 indicating the local pressure distribution across the compression area of the compressed object. It should also be adapted to compare the received pressure values with values regarded as normal/acceptable. Based on that comparison, the controller should be able to calculate a suitable repositioning of the spacing A between the compression plate 4 and the support plate 3 linearly and angularly to provide a suitable local pressure distribution across the compressed object. Further, the controller 15 should be suitable to communicate said information to the displacement device 5 for the latter to actuate the servos 12 to execute the necessary settings and adoptions. Finally, it should be suitable to present the information regarding local pressure information to the operator. The information may by way of example be visualized as a local pressure distribution chart. The visualization may be made on a display (not shown).

The selective distribution of pressure can be realized either as a fully automatic control system or a semi-automatic control system requiring user input, i.e. input from the operator. In one embodiment, the compression plate 4 and/or the support plate may be fitted with electrically operated servos which allows its tilt, i.e. its angular position to be dynamically altered in any direction according to initial pressure information.

The linear and/or angular adaption might be manually altered by the operator using real time information received from the controller. The real time information may by way of example be displayed on a display.

In the following, the operation of the compression device will be discussed. Reference will be made to the flow chart of FIG. 2.

To examine an object, such as a breast, the breast is arranged on the support plate 3, step 100.

The breast is compressed, step 200, by moving the compression plate 4 linearly towards the support plate 3. Thereby the breast will be compressed and flattened between the two plates 3, 4. In its easiest form, the compression is made to reach a pre-set pressure. Thereby a uniform linear spacing A is arranged between the two plates.

The local pressure distribution across the compression area of the compressed breast is determined by the controller, step 300, based on signals received from the plurality of pressure sensors 13. The local pressure distribution may be presented as an image to the operator or be made purely numeric.

The detected local pressure distribution is compared, step 400, to pre-determined acceptable numbers stored in a database. By the comparison it is determined if there is a suitable pressure distribution across the breast. It is also determined whether there is any irrelevant juxtathoracic structures being compressed, such as the pectoralis muscle. In this way the current pressure distribution on the breast during the examination can be measured, achieving a more dynamic compression using an adaptive pressure distribution.

Based on this comparison, a calculation is made to determine, step 500, a suitable linear and angular adaption of the spacing A between the upper surface 6 of the support plate 3 and the lower surface 7 of the compression plate 4 in order of reaching an adequate local pressure distribution across the compressed area of the breast. The determined adjustment of the spacing is made by operating the coupling 11. The selective distribution of pressure may be realized either as a fully automatic control system, i.e. the evaluation is made purely numerical or a semi-automatic system requiring user input. The adjustment to be made may be made manually, semi-automatic or automatic.

By ensuring that pressure is applied to the diagnostically relevant regions of the breast without the compression being hindered by juxtathoracic structures, adequate compression of the breast may be ensured, which in turn will improve the diagnostic accuracy. This will also give the possibility to objectively evaluate the quality of the breast compression in real time during the examination and will give the operator an unprecedented ability to detect and compensate for unsuccessful initial compression. Also, it may be possible to reduce the radiation dose to the patient.

When an adequate local pressure distribution is reached, an x-ray image of the breast is made, step 600.

The adjusted local pressure distribution may be determined anew, step 700, by the plurality of pressure sensors 13.

The compression is released, step 800, by separating the compression plate 4 from the support plate 3 where after the breast may be removed.

The process is repeated until all necessary x-ray images have been made. This may involve tilting of the compression device in view of the stand of the mammographic apparatus.

The result from the mammographic examination proceeding will be presented as an x-ray image of the compressed area of the breast and also a local compression chart across the very same compressed area. The local compression chart may be presented as an image, step 900, with a color or grey scale representing different pressure ranges. It is also possible to use numbers. One such example is disclosed in FIGS. 3a and 3b to be discussed below.

The local pressure chart may be handled as a stand-alone image, but it may also be presented as an image superimposed with the corresponding x-ray image, step 1000.

The pressure data collected when determining adjusted local pressure distribution is compared, step 1100, with pre-defined information regarding tissue elasticity in order of identifying areas of abnormal elasticity in the tissue of the compressed object.

It is to be understood that the x-ray images may be subjected to a suitable image processing to remove any dots resulting from the pressure sensors used.

Figure 3A:
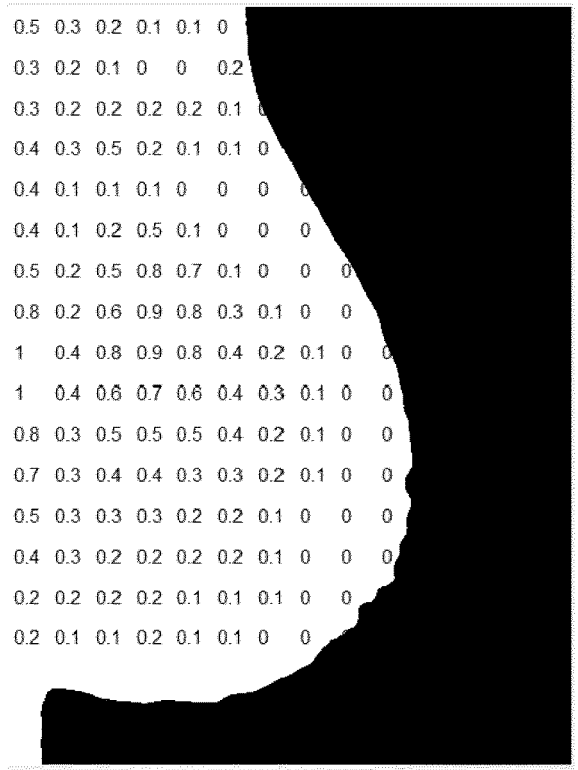
FIG. 3a discloses an example of a pressure distribution chart visualizing an example of an even and good pressure distribution.
Figure 3B:
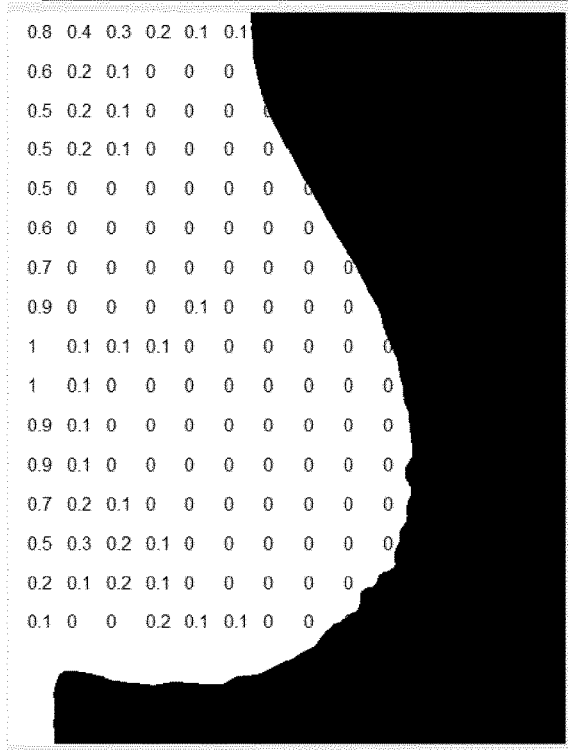
FIG. 3b discloses an example of a pressure distribution chart visualizing an example of an uneven and insufficient pressure distribution.

Now turning to FIGS. 3a and 3b two examples of pressure distribution charts resulting from the present inventive method are disclosed. The pressure distribution is presented numerically with numbers in the range 1-0, where 1 represents the highest pressure and 0 represents the lowest pressure. The charts are based on examination of a population of a number of persons. The chart in FIG. 3a discloses an essentially even pressure distribution across the compressed area of the breast. This is considered to be one example of an acceptable and adequate pressure distribution. The chart in FIG. 3b on the other hand discloses an uneven and considered inadequate pressure distribution with the highest pressure closer to the chest wall and a lower pressure towards the nipple. With such pressure distribution it is recommended to adjust the spacing between the compression plate and the support plate in an angular and/or linear manner to thereby achieve a better pressure distribution.

It goes without saying that the pressure charts disclosed in FIGS. 3a and 3b are only one way of presenting the pressure information. Another possible way may be grey scales or with different colors.

The advantage relative to related modalities such as ultrasound elastography and magnetic resonance elastography lies in the ability to acquire the diagnostic pressure image in conjunction with x-ray mammography, removing the need for separate examinations.

As a short summary, it has been discovered that the elasticity of tissue varies depending on type of tissue. Accordingly any abnormalities in the breast tissue may be detected by studying the visualization of the local pressure distribution chart. Also, it has been discovered that it is possible to differentiate the elasticity in benign tissue changes from malign tissue changes. Accordingly, by the present invention it will, as a complement to the x-ray images be able to improve the detection of any abnormalities in the tissue, and also provide a possibility to mechanically differentiate types of abnormalities. Also, the comfort for the woman will be greatly improved with the ambition that fewer women will refrain from mammographic screenings.

The present invention provides a method to quickly generate a quantitative map of the relative stiffness of the breast during routine mammography screening can have a profound effect on recall rates. The invention gives every woman an additional elastogram, potentially further increasing the diagnostic accuracy.

The compression device may dynamically adjust the local compression according to pressure distribution as given by the plurality of pressure sensors in real time. The adaptable compression plate distributes pressure over relevant regions.

It is advantageous that the compression device is compatible with existing, commercially available mammographic apparatuses.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein.

The foregoing has described the principles, preferred embodiments and modes of operation of the present invention. However, the invention should be regarded as illustrative rather than restrictive, and not as being limited to the particular embodiments discussed above. The different features of the various embodiments of the invention can be combined in other combinations than those explicitly described. It should therefore be appreciated that variations may be made in those embodiments by those skilled in the art without departing from the scope of the present invention as defined by the following claims.

The invention claimed is:

1. Compression device for assisting examination of an object using a field of penetrating radiation, comprising
    a support plate adapted to receive thereon the object to be examined;
    a compression plate;
    a displacement device arranged to interact with the support plate and the compression plate to allow modification of the spacing between the support plate and the compression plate to compress the object therebetween; and
    a plurality of radiolucent pressure sensors distributed across the support plate and/or the compression plate arranged in an array for sensing local pressure distribution at a plurality of locations across the compression area of the compressed object, wherein
    a controller arranged to receive information from the plurality of radiolucent pressure sensors indicating the local pressure distribution across the compression area of the compressed object, and to evaluate the local pressure distribution across the compression area in view of a pre-determined approved pressure distribution, wherein the displacement device is arranged to set and adapt the spacing between the support plate and the compression plate angularly and linearly as a result of the evaluated local pressure distribution across the compression area.

2. A compression device according to claim 1, wherein the spacing between the support plate and the compression plate can be adapted angularly in at least two degrees of freedom.

3. A compression device according to claim 1, wherein the angular and linear spacing between the support plate and the compression plate is arranged to be manually set and adapted.

4. A compression device according to claim 1, wherein the compression plate is segmented into a plurality of segments, each segment of the plurality of segments being individually operable based on information regarding local pressure distribution received from the pressure sensors.

5. A compression device according to claim 1, wherein the displacement device is arranged to dynamically set and adapt the angular and linear spacing between the support plate and the compression plate as a result of the evaluated local pressure distribution.

6. A compression device according to claim 1, wherein:
the support plate and compression plate have object-receiving surfaces facing each other, and
the pressure sensors are detachably arranged as an array on one of the support surfaces of the support plate or compression plate.

7. A compression device according to claim 1, wherein the pressure sensors are disposable.

8. Method of assisting examination of an object using a field of penetrating radiation, comprising
arranging the object to be examined in a compression device, the compression device comprising a support plate and a compression plate and compressing the object therebetween;
determining, by a plurality of radiolucent pressure sensors distributed across the support plate and/or the compression plate in a matrix, the local pressure distribution across the compression area of the compressed object;
evaluating, by a controller, the determined local pressure distribution across the compression area in view of a pre-determined approved pressure distribution; and
adapting the spacing between the support plate and the compression plate angularly and linearly as a result of the evaluated local pressure distribution.

9. The method of claim 8, further comprising the step of determining an adjusted local pressure distribution across the compression area of the compressed area after adapting the spacing.

10. The method of claim 8, further comprising the step of visualizing the local pressure distribution and/or the local adjusted pressure distribution as a pressure distribution chart.

11. The method of claim 8, further comprising the step of taking an x-ray image of the compressed object after adapting the spacing between the support plate and the compression plate.

12. The method of claim 11, further comprising the step of
superimposing the evaluated local pressure distribution with the x-ray image.

13. The method of claim 8, further comprising the step of comparing pressure data collected when determining adjusted local pressure distribution with pre-defined information regarding tissue elasticity in order of identifying areas of abnormal elasticity in the tissue of the compressed object.

14. A compression device according to claim 2, wherein the angular and linear spacing between the support plate and the compression plate is arranged to be manually set and adapted.

15. A compression device according to claim 2, wherein the compression plate is segmented into a plurality of segments, each segment of the plurality of segments being individually operable based on information regarding local pressure distribution received from the pressure sensors.

16. A compression device according to claim 2, wherein the displacement device is arranged to dynamically set and adapt the angular and linear spacing between the support plate and the compression plate as a result of the evaluated local pressure distribution.

17. A compression device according to claim 2, wherein:
the support plate and compression plate have object-receiving surfaces facing each other; and
the pressure sensors are detachably arranged as an array on one of the support surfaces of the support plate or compression plate.

18. The method of claim 9, further comprising the step of visualizing the local pressure distribution and/or the local adjusted pressure distribution as a pressure distribution chart.

19. The method of claim 9, further comprising the step of taking an x-ray image of the compressed object after adapting the spacing between the support plate and the compression plate.

20. The method of claim 19, further comprising the step of
superimposing the evaluated local pressure distribution with the x-ray image.

* * * * *